United States Patent
Chopdekar et al.

(10) Patent No.: US 6,455,727 B1
(45) Date of Patent: Sep. 24, 2002

(54) PROCESS FOR PREPARING CARBETAPENTANE TANNATE

(75) Inventors: Vilas M. Chopdekar, Edison; James R. Schleck, Somerset; Hemant S. Desai, Flemington, all of NJ (US)

(73) Assignee: Jame Fine Chemicals, Inc., Bound Brook, NJ (US)

( * ) Notice: Subject to any disclaimer, the term of this patent is extended or adjusted under 35 U.S.C. 154(b) by 0 days.

(21) Appl. No.: 10/017,136

(22) Filed: Dec. 14, 2001

(51) Int. Cl.$^7$ .................................................. C07C 69/88
(52) U.S. Cl. ...................... 560/102; 514/530; 514/464; 514/653; 514/357; 560/68
(58) Field of Search .................. 560/68, 102; 514/530, 514/464, 653, 357

(56) References Cited

U.S. PATENT DOCUMENTS

| | | | |
|---|---|---|---|
| 5,599,846 A | 2/1997 | Chopdekar et al. | 514/653 |
| 5,663,415 A | 9/1997 | Chopdekar et al. | 560/68 |
| 6,037,358 A | 3/2000 | Gordziel | 514/357 |
| 6,287,597 B1 | 9/2001 | Gordziel | 424/464 |
| 6,306,904 B1 | 10/2001 | Gordziel | 514/530 |

*Primary Examiner*—Paul J. Killos
*Assistant Examiner*—Héctor M Reyes
(74) *Attorney, Agent, or Firm*—Jack Matalon

(57) ABSTRACT

The invention pertains to a process for preparing carbetapentane tannate. The process involves the steps of heating carbetapentane to a temperature of about 80 to about 120° C. and slowly adding tannic acid to the carbetapentane while agitating the reaction mixture. Preferably, no water or any other solvent or diluent is utilized in the process.

9 Claims, No Drawings

PROCESS FOR PREPARING CARBETAPENTANE TANNATE

FIELD OF THE INVENTION

The invention pertains to a process for preparing carbetapentane tannate.

BACKGROUND OF THE INVENTION

Carbetapentane is a well-known commercially available antihistamine. Its chemical name is 2-(diethylaminoethoxy) ethyl-1-phenyl-1-cyclopentanecarboxylate. Carbetapentane is an antitussive compound that is described in U.S. Pat. No. 2,842,845 and is structurally related to caramiphen. Due to its insolubility in water, carbetapentane is typically available in the form of its citrate salt which has a melting of 93° C., and occurs as a white powder which is freely soluble in water and is slightly soluble in alcohol Carbetapentane has an atropine-like action that depresses the cough reflex by selective central nervous system depression. Carbetapentane is frequently combined with one or more antihistaminic drugs such as pyrilamine. Such combination, in the form of their tannate salts is frequently administered orally for the symptomatic relief of coryza associated with the common cold, sinusitis, allergic rhinitis, unproductive cough and upper respiratory tract conditions—see U.S. Pat. No. 6,306,904.

Antihistamine compounds in the form of their free bases as well as their salts, e.g., citrates, maleates, hydrobromides, hydrochlorides, tannates, etc., are well known. Antihistamines in the form of their tannate salts are very desirable because such salts are generally stable and two or more antihistamines is such form may be combined without any untoward side effects.

Tannic acid is commercially available and is used in many industrial applications. It is frequently referred to as gallotannic acid, gallotanin; glycerite or tannin. It is a pale tan powder having a decomposition point of 210–215° C., and is highly soluble in water and alcohols. Its molecular formula is $C_{76}H_{52}O_{46}$ and its CAS number is 1401-55-4. Tannic acid is typically produced from Turkish or Chinese nutgall and has a complex non-uniform chemistry and typically contains about 5–10 wt. % water.

Commercially available antihistamine tannate compositions are relatively impure. Such compositions are typically prepared by reacting the antihistamine free base with tannic acid in the presence of a volatile solvent, usually isopropanol. The yield is only fair (e.g. about 70%) and decomposition products e.g. 2–5 wt. %, and a significant amount of the volatile solvent, e.g. 6–10 wt. %, based on the weight of the composition, remains with the product and cannot be removed.

Typically, in the conventional isopropanol route, the antihistamine free base and the tannic acid will be present in the isopropanol at a concentration of about 20 wt. %, based on the weight of the reaction mixture. The reaction mixture is stirred for about one hour, while maintaining a temperature of 60–70° C. The reaction mixture is cooled to room temperature and filtered. The precipitate is vacuum dried for an extended period of time at a temperature of 60–80° C. A yield of product of only about 70% is obtained and the product purity will be about 85–90 wt. %, based on the weight of the composition (the impurities consist of isopropanol and decomposition products which cannot be removed).

Many antihistamine tannates are heat sensitive and therefore undergo decomposition quite readily upon prolonged exposures to temperatures as low as 50° C. Accordingly, even when the solvent utilized in its preparation has a relatively high vapor pressure such as is in the case of isopropanol, it is impossible to reduce the solvent content below about 6 wt. %, based on the weight of the antihistamine tannate composition, even at reduced pressures and very mild elevated temperatures. Moreover, from an environmental point, it would be most desirable if the antihistamine tannate could be prepared such that the use of volatile solvents could be avoided.

The process disclosed in U.S. Pat. No. 5,663,415 represents a significant improvement over the isopropanol route. The process disclosed in the '415 patent involves three steps:

(a) the antihistamine in the form of its free base is contacted with tannic acid in the presence of water at a maximum temperature which will not cause decomposition of the antihistamine tannate to an extent of greater than about 5 wt %, based on the weight of the antihistamine tannate;

(b) the antihistamine is allowed to remain in contact with the tannic acid in the presence of water for a period of time of about 5 minutes to 4 hours at said maximum temperature; and (c) the antihistamine tannate resulting from step (b) freeze-dried at a temperature and at a reduced pressure and for such period of time that (i) at least about 90 wt. % of the water is removed from the antihistamine tannate and (ii) decomposition of the antihistamine tannate will be limited to a maximum of about 5 wt. %.

The '415 patent discloses a three-step method that results in the production of pure antihistamine tannate compositions having a minimum purity level of at least 90 wt. %, usually at least 95 wt. % and often at least 98 wt. %, based on the weight of the composition, with a yield of at least about 90% and often with a yield in excess of 97%.

The chief "impurity" present in the compositions prepared by the process of the '415 patent is water which is present in an amount of 1–5 wt. %, based on the weight of the composition.

Although the process disclosed in the '415 patent represents a dramatic improvement leading to very pure antihistamine tannate compositions, it has several drawbacks: freeze-drying is quite time-consuming(typically 30–36 hours to remove 1 liter of water) and expensive and requires specialized equipment in order to achieve the reduced pressures and temperature required to dry the antihistamine tannate composition, i.e., a pressure of not greater than about 500 miliTorr and a temperature in the range of about −60° C. to −20° C. Such specialized equipment also limits the amount of product that can be processed within a reasonable amount of time.

DETAILS OF THE INVENTION

It has now been found that very pure carbetapentane tannate may be produced by a synthetic route which overcomes the drawbacks of the isopropanol and freeze-drying routes discussed above. The process of the invention avoids the use of aqueous and/or non-aqueous solvents or diluents and permits the rapid, inexpensive production of carbetapentane tannate having a purity level in excess of about 95 wt. %, and quite often a purity level in excess of 98 wt. %.

For the purposes of this invention, it is to be understood that the term "carbetapentane" refers to the free base which is employed as the starting material in the process of the invention. If the carbetapentane is present in the form of a salt (typically a citrate), the salt is neutralized with a stoichiometric amount of a base such as sodium or potassium hydroxide and the resulting carbetapentane layer is washed free of salts.

The process of the invention involves the following steps:

(a) carbetapentane is heated to a temperature of up to about 120° C.; and (b) tannic acid is added to the carbetapentane while agitating the reaction mixture.

Preferably, the temperature of the carbetapentane is maintained in the range of about 80 to about 100° C., e.g., 85 to 95° C., during the addition of the tannic acid. In general, the tannic acid is slowly (e.g., over a period of 5 to 30 minutes) added to the carbetapentane which is continually agitated while the temperature is maintained in such range. Preferably, the reaction mixture is agitated for an additional period of about 10 minutes to about 2 hours after all of the tannic acid has been added to the carbetapentane, during which time such temperature range is maintained.

In general, the carbetapentane will be employed in an amount of about 1 to about 5 moles, preferably 2 to 4 moles, of carbetapentane per mole of tannic acid. If the reaction mixture proves to be too viscous for efficient agitation to occur, a small amount of water, e.g., 1–5 wt. %, may be added to the reaction mixture. However, it is preferred that the reaction between the carbetapentane and the tannic acid be carried out in the substantial absence of any aqueous or non-aqueous solvent or diluent.

The reaction mixture is subsequently cooled to room temperature and is thereafter milled to provide a free-flowing powder having a particle size in the range of about 50 to about 200 mesh. The resultant carbetapentane tannate is a light tan-colored powder having a softening point of 80–85° C., a minimum purity of at least about 95 wt. % and it will be slightly soluble in water and soluble in alcohols and insoluble in methylene chloride. In contrast thereto, carbetapentane (free base) is a liquid which is insoluble in water, but is soluble in alcohols and methylene chloride, while tannic acid is a tan-colored powder is soluble in water and alcohols, but is insoluble in methylene chloride, while tannic acid has a decomposition point of 210–215° C.

The carbetapentane tannate produced by the process of the invention may be used as is in antitussive pharmaceutical preparations or, if desired, it may be formulated with other pharmaceutically active ingredients such as antihistamines and antitussives, e.g., chlorpheniramine, brompheniramine, pyrilamine, phenylephrine, ephedrine, pseudo-ephedrine, dextromethorphan, guaifenesin, carbinoxamine, and the like. Typically, these other active ingredients will be employed in the form of their free bases or their salts, e.g., citrates, maleates, hydrobromides, hydrochlorides, tannates, etc.

The following nonlimiting examples will serve to illustrate the present invention.

EXAMPLE 1

A 500 cc resin flask was fitted with a stirrer, thermometer, nitrogen blanket and a hot water bath. Carbetapentane (free base obtained by stoichiometric neutralization of carbetapentane citrate with sodium hydroxide) in the amount of 72.5 g (0.2174 m) was placed in the flask and was heated to a temperature of about 90–100° C., with stirring, over a 10-minute period. Thereafter, while maintaining stirring and a temperature of about 90–100° C., tannic acid in the amount of 123.3 g (0.0725 m) was added to the flask over a 15-minute period. Stirring and a temperature of 90–100° C. were continued for an additional 30-minute period after all of the tannic acid had been added. The reaction mixture was then cooled to room temperature and milled to yield 188 g (96% of theory) a fine powder of carbetapentane tannate In order to determine whether the carbetapentane free base had fully reacted with the tannic acid, a 2 g aliquot sample of the fine powder was mixed with 110 g of methylene chloride in a beaker for 10 minutes. The mixture was filtered and the filtrate was evaporated to dryness, yielding a residue of only 2 mg. The precipitate was dried and weighed 1.98 g, thus indicating that a complete reaction had taken place between the carbetapentane (free base) and the tannic acid in accordance with the process of the invention.

What is claimed is:

1. A process for preparing carbetapentane tannate which comprises the steps of:

(a) heating carbetapentane to a temperature of up to about 120° C.; and (b) adding tannic acid to the carbetapentane while agitating the reaction mixture.

2. The method of claim 1 wherein the temperature of the carbetapentane is maintained in the range of about 80 to about 100° C. during the addition of the tannic acid.

3. The method of claim 2 wherein the temperature is maintained in the range of 85 to 95° C.

4. The method of claim 3 wherein the carbetapentane is employed in an amount of about 1 to about 5 moles of carbetapentane per mole of tannic acid.

5. The method of claim 4 wherein the carbetapentane is employed in an amount of 2 to 4 moles of carbetapentane per mole of tannic acid.

6. The method of claim 1 wherein the reaction mixture is agitated for an additional period of about 10 minutes to about 2 hours after all of the tannic acid has been added to the carbetapentane, while maintaining the reaction mixture at a temperature of up to about 120° C.

7. The method of claim 1 wherein the process is carried out in the substantial absence of any aqueous or non-aqueous solvent or diluent.

8. The method of claim 1 wherein the carbetapentane tannate obtained from step (b) is milled to provide a free-flowing powder.

9. The method of claim 8 wherein the powder has a particle size in the range of about 50 to about 200 mesh.

* * * * *